(12) United States Patent
Larson

(10) Patent No.: US 8,192,569 B2
(45) Date of Patent: Jun. 5, 2012

(54) MEDICAL DEVICES AND METHODS OF MAKING THE SAME

(75) Inventor: Blane Larson, Monticello, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/907,742

(22) Filed: Oct. 19, 2010

(65) Prior Publication Data

US 2011/0030876 A1 Feb. 10, 2011

Related U.S. Application Data

(62) Division of application No. 10/847,688, filed on May 18, 2004, now Pat. No. 7,815,624.

(51) Int. Cl.
*B29C 65/00* (2006.01)
*B29C 65/16* (2006.01)

(52) U.S. Cl. .................. 156/60; 156/272.2; 156/272.8; 348/164; 604/103

(58) Field of Classification Search ............ 156/272.2, 156/60, 272.8; 348/164; 604/103
See application file for complete search history.

(56) References Cited

U.S. PATENT DOCUMENTS

| | | | |
|---|---|---|---|
| 3,588,347 A * | 6/1971 | Montone et al | 348/164 |
| 4,251,305 A * | 2/1981 | Becker et al. | 156/86 |
| 4,578,173 A | 3/1986 | Seshimoto | |
| 4,590,028 A | 5/1986 | Rosenkranz et al. | |
| 4,636,609 A | 1/1987 | Nakamata | |
| 4,755,649 A | 7/1988 | Barker et al. | |
| 4,838,881 A | 6/1989 | Bennett | |
| 5,152,277 A | 10/1992 | Honda | |
| 5,209,729 A | 5/1993 | Hofmann et al. | |
| 5,395,336 A | 3/1995 | Barclay | |
| 5,413,559 A | 5/1995 | Sirhan et al. | |
| 5,423,754 A | 6/1995 | Cornelius et al. | |
| 5,501,759 A | 3/1996 | Forman | |
| 5,531,721 A | 7/1996 | Pepin et al. | |
| 5,558,737 A | 9/1996 | Brown et al. | |
| 5,772,641 A | 6/1998 | Wilson | |
| 5,876,376 A | 3/1999 | Schwab et al. | |
| 5,893,959 A * | 4/1999 | Muellich | 156/272.8 |
| 5,951,929 A | 9/1999 | Wilson | |
| 5,980,505 A | 11/1999 | Wilson | |
| 6,103,037 A | 8/2000 | Wilson | |
| 5,912,463 A * | 9/2000 | Kawauchi et al. | 250/338.1 |
| 6,117,613 A * | 9/2000 | Kawauchi et al. | 430/270.1 |
| 6,168,588 B1 | 1/2001 | Wilson | |
| 6,197,015 B1 | 3/2001 | Wilson | |
| 6,199,262 B1 | 3/2001 | Martin | |
| 6,323,413 B1 | 11/2001 | Roth et al. | |

(Continued)

FOREIGN PATENT DOCUMENTS

EP 0362497 B1 3/1996

(Continued)

OTHER PUBLICATIONS

The Vision Show West, Nov. 18-21, 2002, Santa Clara, CA, pp. 1-55.

*Primary Examiner* — Richard Crispino
*Assistant Examiner* — Elizabeth Royston
(74) *Attorney, Agent, or Firm* — Seager, Tufte & Wickhem, LLC

(57) ABSTRACT

Medical devices and related methods are disclosed.

14 Claims, 4 Drawing Sheets

U.S. PATENT DOCUMENTS

| | | |
|---|---|---|
| 6,447,479 B1 | 9/2002 | Nobuyoshi et al. |
| 6,503,353 B1 | 1/2003 | Peterson et al. |
| 6,511,462 B1 | 1/2003 | Itou |
| 6,596,217 B1 | 7/2003 | Davis-Lemessy et al. |
| 6,656,315 B2 | 12/2003 | Sallavanti |
| 2002/0115963 A1 | 8/2002 | Clarke et al. |
| 2002/0144984 A1* | 10/2002 | Mori et al. ............ 219/121.64 |
| 2003/0050686 A1 | 3/2003 | Raeder-Devens et al. |
| 2003/0093107 A1 | 5/2003 | Parsonage et al. |
| 2005/0043679 A1 | 2/2005 | Devens, Jr. et al. |

FOREIGN PATENT DOCUMENTS

| | | |
|---|---|---|
| WO | 03064140 A2 | 8/2003 |

* cited by examiner

MEDICAL DEVICES AND METHODS OF MAKING THE SAME

CROSS-REFERENCE TO RELATED APPLICATION

This application is a divisional of U.S. patent application Ser. No. 10/847,688, filed May 18, 2004, now U.S. Pat. No. 7,815,624, the entire disclosures of which is hereby incorporated by reference.

TECHNICAL FIELD

The invention relates to medical devices and related methods.

BACKGROUND

A balloon catheter is one type of medical device that can be introduced into the body to treat various conditions. For example, the balloon catheter can be used to treat conditions of the heart (such as in balloon coronary angioplasty or stent delivery) or to treat non-vascular conditions (such as obstructions of the gall bladder or bile duct).

A balloon catheter typically includes an elongated shaft and an inflatable balloon carried by the shaft. The shaft includes a lumen in fluid communication with the interior of the balloon. During use, the balloon is in a deflated condition so that it can be delivered through a narrow, tortuous path to a target site. At the target site, the balloon can be inflated by introducing a fluid, such as a liquid or a gas through the lumen of the shaft and into the balloon. Subsequently, the balloon catheter can be removed by removing the fluid, thereby deflating the balloon and withdrawing the catheter.

In stent delivery, a stent is compacted onto the balloon and transported to a target site. Upon reaching the site, the balloon can be expanded, thereby deforming and fixing the stent at a predetermined position (e.g., in contact with the vessel wall). The balloon can then be collapsed and withdrawn.

SUMMARY

In one aspect, the invention features a method of making a catheter, the method including overlapping a first component of the catheter and a second component of the catheter, and applying infrared radiation and visible light to the first and second components to align the first and second components.

In another aspect, the invention features a method of making a catheter, the method including joining a first component of the catheter and a second component of the catheter, and applying a first form of electromagnetic radiation to the first and second components. The first form of electromagnetic radiation is capable of penetrating through at least one of the first and second components. The method further includes applying a second form of electromagnetic radiation to the first and second components. The second form of electromagnetic radiation reflects off of at least one of the first and second components.

In an additional aspect, the invention features a method of making a catheter, the method including joining a first component of the catheter with a second component of the catheter by forming a lap weld between the first and second components. The lap weld has a predetermined tolerance of less than about two millimeters. The first component has a first color and the second component has a second color that is different from the first color.

In a further aspect, the invention features a medical device that includes a catheter with a first component of a first color and a second component of a second color that is different from the first color. The first and second components are joined by a lap weld.

In another aspect, the invention features a method of making a catheter, the method including overlapping a first component of the catheter and a second component of the catheter, and applying infrared radiation to the first and second components to align the components.

Embodiments of aspects of the invention may include one or more of the following features.

The method can further include forming a lap weld between the first and second components. The lap weld can be formed within a predetermined tolerance of about two millimeters or less (e.g., about 0.0127 millimeter or less, about 0.000635 millimeter or less). The lap weld can have a length of from about 3.0 millimeters to about 5.0 millimeters, and/or a thickness of from about 0.0012 inch to about 0.011 inch.

The method can further include applying at least two sources of visible light to the first and second components. At least one of the visible light sources can provide visible light with a wavelength of from about 575 nanometers to about 700 nanometers. Alternatively or additionally, at least one of the visible light sources can provide visible light with a wavelength of from about 491 nanometers to about 575 nanometers. Alternatively or additionally, at least one of the visible light sources can provide visible light with a wavelength of from about 400 nanometers to about 491 nanometers. The method can further include detecting the infrared radiation and visible light with a detector (e.g., a charge-coupled device, a CMOS, an InGaAs photodetector), and/or controlling the infrared radiation and/or visible light with a controller. The infrared radiation can have a wavelength of from about 800 nanometers to about 1000 nanometers (e.g., about 880 nanometers). The infrared radiation and/or the visible light can be generated by one or more LED's.

The first component can be an inner portion, an outer portion, a tip (a bumper tip), or a balloon. The first component can be a proximal outer portion and the second component can be a distal outer portion. The first component can be a balloon and the second component can be a distal outer portion. The first component can be an inner portion and the second component can be a tip. The first component can be a balloon and the second component can be an inner portion. The contrast between the first component and the second component can be more than about ten percent (e.g., more than about 20 percent, more than about 30 percent). The first component can have one color and the second component can have another color that can be the same as, or different from, the color of the first component. The color of the first component can correspond to light having a wavelength of from about 491 nanometers to about 700 nanometers. The color of the second component can correspond to light having a wavelength of from about 400 nanometers to about 491 nanometers. The first component can include a polymer, and/or the second component can include a polymer that can be the same as, or different from, the polymer of the first component. The polymer can be a nylon or a polyether-polyamide block copolymer.

The catheter can be a balloon catheter. The catheter can be a rapid exchange catheter. The catheter can have a burst pressure of more than about 235 psi. Embodiments may have one or more of the following advantages. The method can be used to form lap welds of a predetermined tolerance between one or more components of a medical device. A lap weld formed between medical device components can be formed in compliance with an industry standard (e.g., a critical alignment standard). A lap weld can provide a strong bond between medical device components, and can reduce the likelihood of detachment of the medical device components (e.g., during delivery or use). The method can be used to accurately align medical device components that may not be accurately aligned by using visible light alone. Complex medical device components can be aligned accurately and relatively inexpensively. Alignment of medical device components can be automated. Differently colored medical device components can be joined together with a lap weld. The method can enhance (e.g., by more than about 20 percent) the contrast between differently colored medical device components. The color of a medical device component can, for example, provide information about the properties (e.g., type, thickness, composition) of the medical device component. A physician using a medical device with differently colored components can ascertain the location of joints (e.g., lap welds) between the components (e.g., the location of a joint between a tip and a balloon waist). A physician can easily pass a colored catheter over a guidewire, e.g., relative to a comparable clear catheter.

Other aspects, features, and advantages of the invention will be apparent from the description of the preferred embodiments thereof and from the claims.

DETAILED DESCRIPTION

Figure 1A:
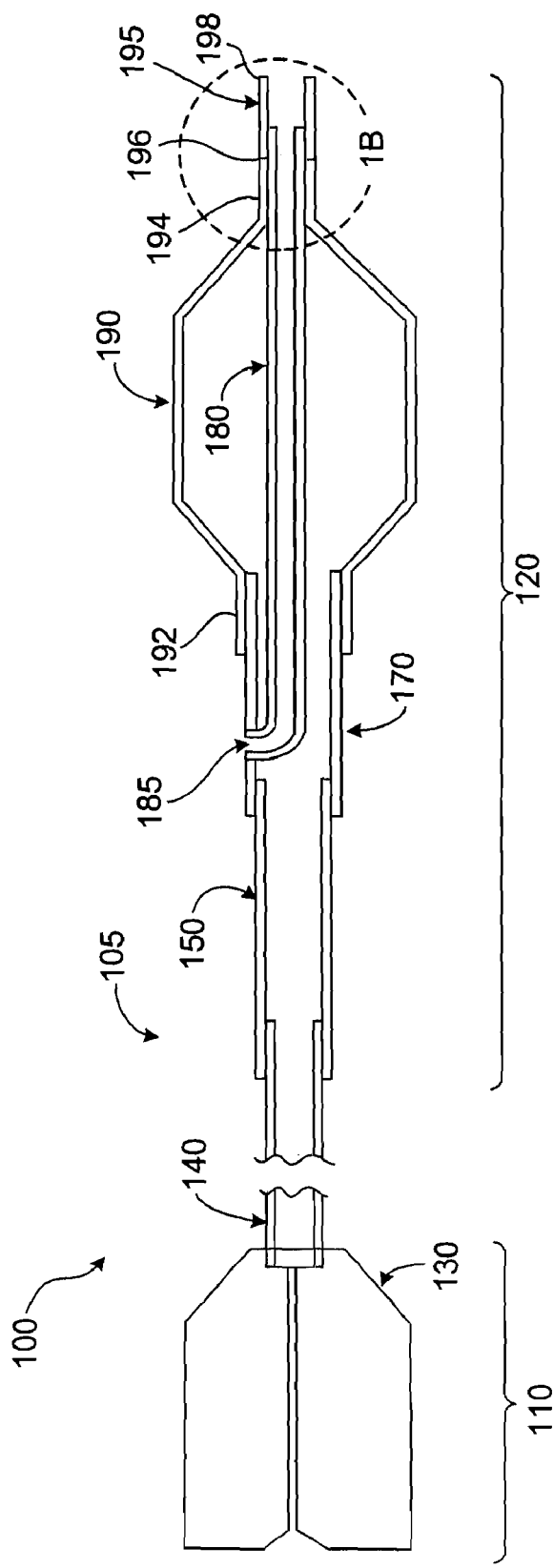
FIG. 1A is a cross-sectional side view of an embodiment of a balloon catheter.

Referring to FIG. 1A, a rapid-exchange balloon catheter 100 includes a catheter shaft 105 having a proximal end 110 and a distal end 120, and a balloon 190 carried by the catheter shaft at the distal end. Catheter shaft 105 includes a proximal outer portion 150, a distal outer portion 170 connected to the proximal outer portion, and a distal inner portion 180 connected to the proximal outer portion. Distal inner portion 180 defines a port 185 in distal outer portion 170. At proximal end 110, balloon catheter 100 includes a manifold 130 connected to proximal outer portion 150 by a sheath 140, e.g., for a hypotube (not shown). At distal end 120, balloon catheter 100 includes a tip 195 having a proximal end 196 and a distal end 198. Balloon 190 is connected to distal outer portion 170 and distal inner portion 180 by waist regions 192 and 194, respectively. Examples of commercially available balloon catheters with this general configuration include the Monorail family of balloon catheters (Boston Scientific-SciMed, Maple Grove, Minn.).

Balloon catheter 100 can be used as follows. An operator of balloon catheter 100 delivers distal end 120 of balloon catheter 100 into a body lumen (e.g., a blood vessel) over an emplaced guidewire. Balloon catheter 100 is navigated through the lumen to position balloon 190 at a treatment site. Once balloon 190 reaches the treatment site, balloon 190 is inflated with inflation fluid, so that balloon 190 contacts the wall of the lumen. Thereafter, balloon 190 is deflated and removed from the lumen. Alternatively or additionally, balloon 190 can be used to deliver a medical device (e.g., a stent, a graft) and/or to block a passageway.

Figure 1B:
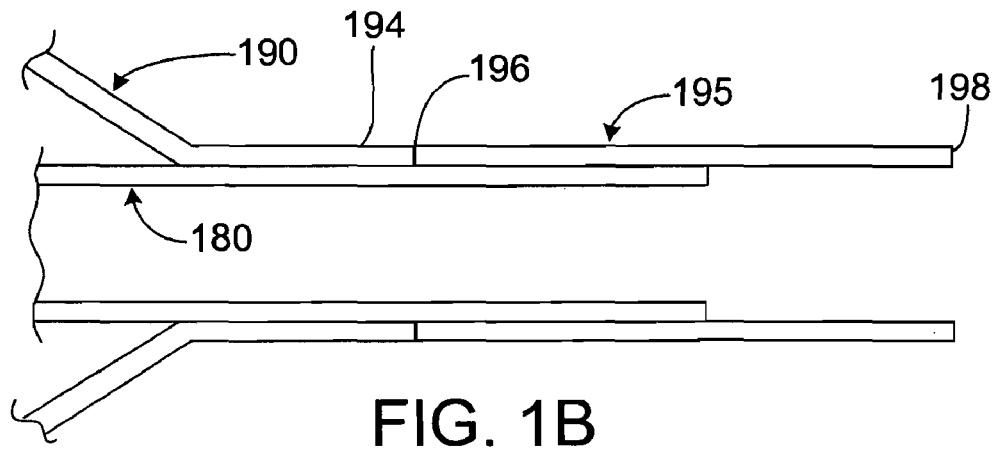
FIG. 1B is an enlarged view of region IB in FIG. 1A.

Referring now to FIG. 1B, distal inner portion 180 is bonded to both waist region 194 of balloon 190, and to the proximal portion of tip 195. Tip 195 and distal inner 180 are different colors (e.g., tip 195 is purple and distal inner portion 180 is green). The bond between distal inner portion 180 and tip 195 is a lap bond, in which portions of components (as shown, the distal inner portion and the tip) overlap.

Figure 2A:
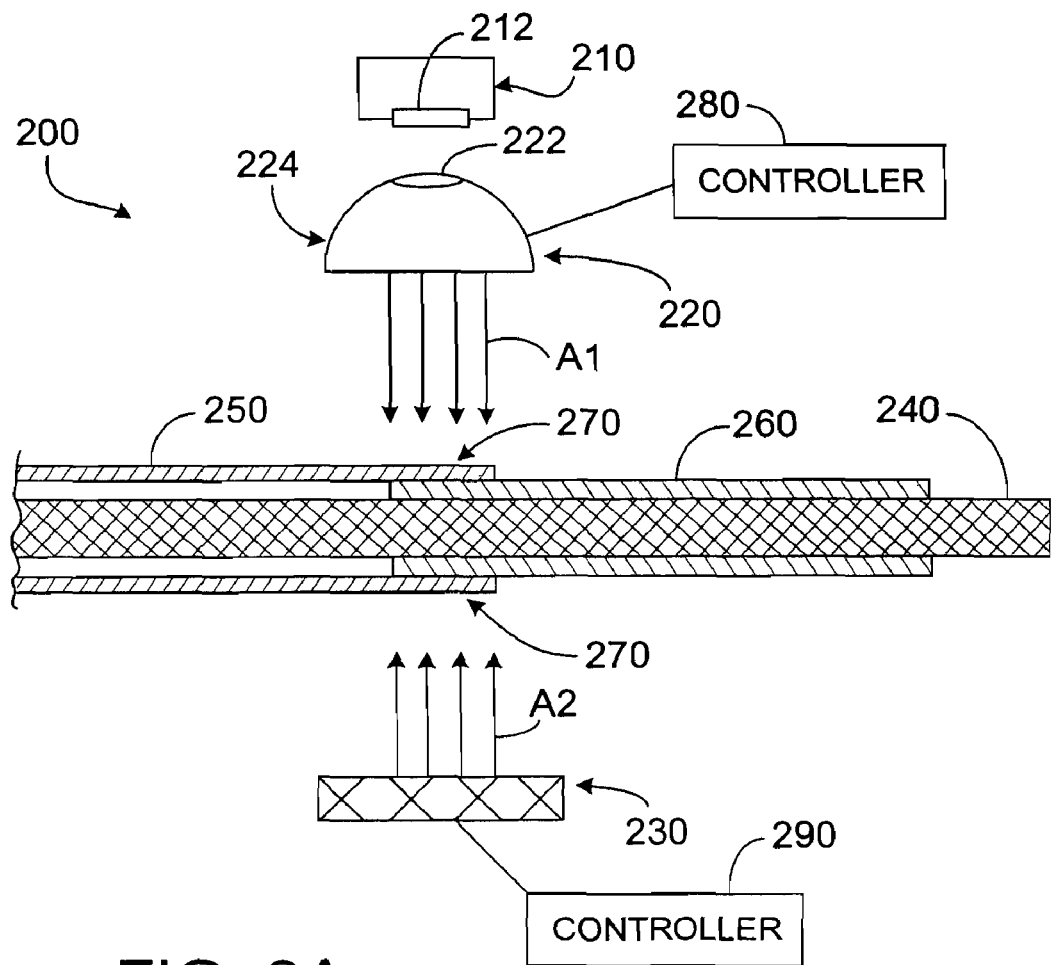
FIG. 2A is an illustration of an embodiment of a system for joining two or more medical device components.

FIG. 2A shows an apparatus 200 for lap bonding two components, such as two components of different color, light, reflectivity, and/or light transmissivity. Apparatus 200 is capable of providing transmissive light, such as infrared radiation, and reflective light, such as visible light. The transmissive light is capable of penetrating one or more components to enhance contrast and/or visibility of the component(s), particularly where the components overlap. The reflective light is capable of enhancing contrast and/or visibility of the surfaces of the components. As shown, apparatus 200 includes a back light 230 for providing transmissive light, and a dome light 220 for providing reflective light. Back light 230 is controlled by a controller 290, and dome light 220 is controlled by a controller 280. Dome light 220 has a hole 222 in its domed surface 224. Apparatus 200 further includes a camera 210 having a lens 212 that is aligned to focus through hole 222.

During use, two differently colored tubular catheter components 250 and 260 (such as a tip and a distal inner portion) can be aligned and bonded by placing the components between dome light 220 and back light 230. As shown, components 250 and 260 are loaded onto mandrel 240 so that the components are located between dome light 220 and back light 230. Part of component 260 is placed within component 250, forming an overlap region 270. Dome light 220 provides visible light (represented by arrows A1) to overlap region 270, and back light 230 provides infrared radiation (represented by arrows A2) to overlap region 270. The wavelengths of the visible light and the infrared radiation are selected to render component 260 visible through component 250 at overlap region 270. As a result, an operator viewing overlap region 270 through camera 210 can adjust the amount of overlap between components 250 and 260 to achieve a desired amount of overlap with good precision and accuracy. If component 260 is not sufficiently visible through component 250, then the operator can use controller 280 to adjust the visible light from dome light 220, and/or controller 290 to adjust the infrared radiation from back light 230.

Visible light from dome light 220 is selected to reflect off of components 250 and 260. Dome light 220 can include one source of visible light, or multiple sources of visible light (e.g., an array of light-emitting diodes (LED's)). For example, dome light 220 can include three LED's: a red LED, a green LED, and a blue LED. The current flow through each LED can be selected to produce the desired intensity of light from the particular LED, and/or can depend on the particular controller used to control the LED. In some embodiments, the current flow through an LED can be about 150 mA or less (e.g., when the LED is controlled by an S-6000 controller, from Advanced Illumination (Rochester, Vt.), with an input voltage of about 30 Volts or less). In certain embodiments, the current flow through an LED can be about 100 mA or less (e.g., about 90 mA). In some embodiments, the current flow through an LED can be about 70 mA or less (e.g., about 50 mA, about 60 mA). In a preferred embodiment, dome light 220 includes an array of red and green LED's, with a current of about 90 mA flowing through the red LED's and a current of about 50 mA flowing through the green LED's (e.g., when an S-6000 controller controls the LED's). Examples of dome lights include the model DL7248 RGB Diffuselight, available from Advanced Illumination (Rochester, Vt.).

Infrared radiation from back light 230 is selected to penetrate certain pigmented polymers, such as the polymer(s) from which component 250 is formed. Back light 230 can include one source of infrared radiation, or multiple sources of infrared radiation. Sources of infrared radiation that can be used in back light 230 include, for example, LED's and lasers. In embodiments, infrared radiation from back light 230 can have a wavelength of from about 800 nanometers to about 1000 nanometers (e.g., about 880 nanometers, about 940 nanometers). In a preferred embodiment, infrared radiation from back light 230 has a wavelength of about 880 nanometers. Examples of back lights include the model BL1520 880 nm back light, available from Advanced Illumination (Rochester, Vt.).

Camera 210 can be used to detect the combined effect of the visible light and the infrared radiation on components 250 and 260, particularly on overlap region 270. Camera 210 can be, for example, the model Legend 544C camera, available from DVT Sensors (Duluth, Ga.). While a camera is shown, other types of detectors can be used in apparatus 200, such as complementary metal-oxide-semiconductors (CMOS), charge-coupled devices (CCD's), and/or InGaAs photodetectors.

As described above, an operator can use apparatus 200 to enhance the contrast between component 250 and component 260, and thereby to enhance the view of the position of component 260 within component 250. The percentage contrast between two or more components can be determined, for example, by measuring an intensity or contrast gradient across the region of interest. The intensity or contrast gradient can be determined by calculating the rate of change (i.e., the first-order derivative) across the region of interest using software applications (e.g., Frameworks, available from DVT Sensors, Duluth, Ga.) that are bundled with camera 210.

The percentage contrast between component 250 and component 260 at overlap region 270 can be from about five percent to about 50 percent. In some embodiments, the percentage contrast between component 250 and component 260 at overlap region 270 can be more than about five percent (e.g., more than about ten percent, more than about 20 percent, more than about 30 percent, more than about 40 percent).

An operator of apparatus 200 can adjust the visible light from dome light 220 and/or the infrared radiation from back light 230 by using controllers 280 and 290, which can control the intensity of radiation emitted from dome light 220 and/or back light 230. Examples of controllers include the model S6000 electronic controller, available from Advanced Illumination (Rochester, Vt.).

Figure 2B:
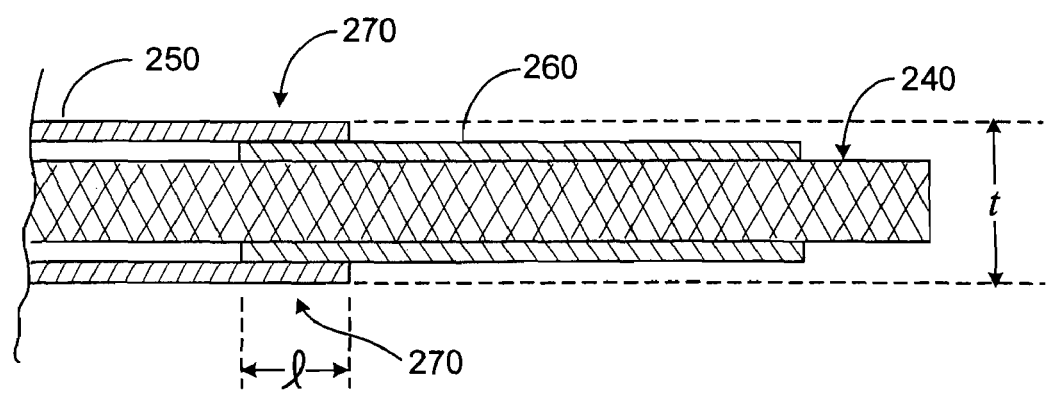
FIG. 2B is an illustration of a portion of the system shown in FIG. 2A.

Referring to FIG. 2B, overlap region 270 can have a length "l" of from about 3.0 millimeters to about 5.0 millimeters (e.g., about 3.5 millimeters, about 4.375 millimeters), and/or a thickness "t" of from about 0.0012 inch to about 0.011 inch (e.g., about 0.00725 inch, about 0.008 inch). By using the apparatus shown in FIG. 2, an operator can form an overlap region 270 to a predetermined tolerance of about two millimeters or less (e.g., about 0.0127 millimeter or less, about 0.000635 millimeter or less).

Components 250 and 260 can be any of a number of different colors. In some embodiments, at least one or both of components 250 and 260 can be blue, red, green, orange, yellow, or purple. As an example, component 250 can be purple and component 260 can be green. As another example, component 250 can be red and component 260 can be green. In some embodiments, a component (such as component 260) that is partially disposed within another component can be black. For example, component 260 can be black, and component 250 can be blue. A medical device component can be rendered black with the addition, for example, of a carbon composition. Component 250 and/or component 260 can have a color that corresponds to light with a wavelength of about 700 nanometers, about 600 nanometers, about 580 nanometers, about 500 nanometers, about 450 nanometers, or about 400 nanometers.

A medical device assembled using the above-described process can be a catheter, such as an over-the-wire catheter or a rapid-exchange catheter. The medical device can be an endoprosthesis-delivery catheter (e.g., a stent delivery catheter), and/or a balloon catheter. An endoprosthesis delivered by the medical device can be self-expanding or can be balloon-expandable.

Components joined by the process of FIG. 2A can include pairs of, for example, inner portions, outer portions, tips (bumper tips), and/or balloons. Examples of pairs of components include a proximal outer portion and a distal outer portion; a proximal balloon waist and a distal outer portion; an inner portion and a tip; an inner portion and an outer portion; and a distal balloon waist and an inner portion.

The components can be made of one or more polymers, and can be made of the same polymers or different polymer(s). Examples of polymers include thermoplastics and thermosets. Examples of thermoplastics include polyolefins, polyamides (e.g., nylon 12, nylon 11 (e.g., Duralon®), nylon 6/12, nylon 6, nylon 66), polyesters (e.g., polyterephthalate (PET)), polyethers, polyurethanes, polyvinyls, polyacrylics, fiuoropolymers, copolymers and block copolymers thereof, such as block copolymers of polyether and polyamide (e.g., Pebax®), and combinations thereof. Examples of thermosets include elastomers such as EPDM, epichlorohydrin, polyureas, nitrile butadiene elastomers, silicones, expoxies and isocyanates. Biocompatible thermosets may also be used, and these include, for example, biodegradable polycaprolactone, poly(dimethylsiloxane)-containing polyurethanes and ureas, and polysiloxanes. Other polymers are described in commonly assigned U.S. Ser. No. 10/645,055, filed Aug. 21, 2003.

In addition to polymer(s), the components can further include one or more additives that can enhance formation of a composite. For example, the components can include one or more coupling or compatibilizing agents, dispersants, stabilizers, plasticizers, surfactants, and/or pigments. Examples of additive(s) are described in U.S. Patent Application Publication 2003/0093107.

In embodiments, one or more of the components of a medical device can be formed of a polymer with a Shore D hardness of about 75 durometer or less (e.g., about 70 durometer or less, about 65 durometer or less, about 60 durometer or less). In embodiments, the polymer can have a Shore D hardness of about 50 durometer or more. Examples of such polymers include Pebax® 7233, Pebax® 7033, and Pebax® 6333. Without wishing to be bound by theory, it is believed that a lap bond allows relatively soft polymers to be used without compromising, e.g., burst strength. In some embodiments, a medical device including lap-welded components formed of relatively soft polymers can exhibit enhanced burst pressure. In certain embodiments, medical devices (e.g., catheters) formed by the above-described process can have a burst pressure of more than about 235 psi (e.g., from about 235 psi to about 310 psi). In some embodiments, the medical devices can have a burst pressure of more than about 265 psi (e.g., more than about 309 psi, more than about 310 psi).

The following example is intended to be illustrative and not limiting.

EXAMPLE

A lap weld was formed between a tip and a distal inner portion as follows.

A green tri-layer distal inner portion (including an inner layer formed of HDPE Marlex® 4903, an intermediate layer formed of Plexar® PX-380, and an outer layer formed of Pebax® 7233) was loaded onto a diamond drawn 304 stainless steel mandrel. The distal inner portion had a length of about 12 inches, an inner diameter of about 0.0166 inch, and an outer diameter of about 0.0236 inch.

A pink tip formed of Grilamid® ELY 2694 (from EMS Grivory, EMS-CHEMIE (North America) Inc., Sumpter, S.C.) was then loaded onto the mandrel. The proximal end of the tip was disposed over the distal end of the distal inner portion, to form an overlap region with a length of about four millimeters and a width of about 0.028 inch. The tip had a length of about 4.5 millimeters, an inner diameter of about 0.0246 inch, and an outer diameter of about 0.0284 inch.

A back light (model BL1520, from Advanced Illumination, Rochester, Vt.) including an array of LED's was disposed beneath the mandrel, such that infrared radiation from the back light shone up onto the mandrel. The back light was about ten millimeters below the mandrel.

A dome light (a model DL7248 RGB Diffuselight, from Advanced Illumination, Rochester, Vt.) was disposed above the mandrel, such that visible light from the dome light shone down onto the mandrel. The dome light was about three centimeters above the mandrel. The dome light was formed of an array of LED's, including multiple red LED's, multiple blue LED's, and multiple green LED's.

A color camera (model DVT Legend 544C, from DVT Sensors, Duluth, Ga.) with a Tamron Lens (from Tamron USA, Inc., Commack, N.Y.) was disposed above the dome light, such that the lens was in alignment with a hole in the domed surface of the dome light. Down tubes, also known as extension tubes (from DVT Sensors, Duluth, Ga.), were attached to the lens to extend the focal length of the lens and enhance magnification of the overlap area.

A controller (model S-6000, from Advanced Illumination, Rochester, Vt.) was used to control the infrared radiation from the back light and the visible light from the dome light.

Infrared radiation having a wavelength of about 880 nanometers was directed from the back light to the overlap region, for a period of about 15 seconds. At the same time, visible light from the dome light was directed to the overlap region, for a period of about 15 seconds. The red LED's in the dome light had a current flow of about 90 mA, the green LED's in the dome light had a current flow of about 50 mA, and the blue LED's in the dome light had no current flow. While the infrared radiation and the visible light were directed to the overlap region, the contrast between the tip and the distal inner portion was about 30 percent. The overlap region was aligned to have a length of about 4.0 millimeters and a width of about 0.0284 inch.

A lap weld was formed at the overlap region using a 10-watt Synrad Series 48 CO2 laser (Synrad, Inc.). The laser was applied to the overlap region for a period of about three seconds. Laser bonding systems and processes are described, for example, in Forman, U.S. Pat. No. 5,501,759, which is hereby incorporated by reference in its entirety.

Figure 3:
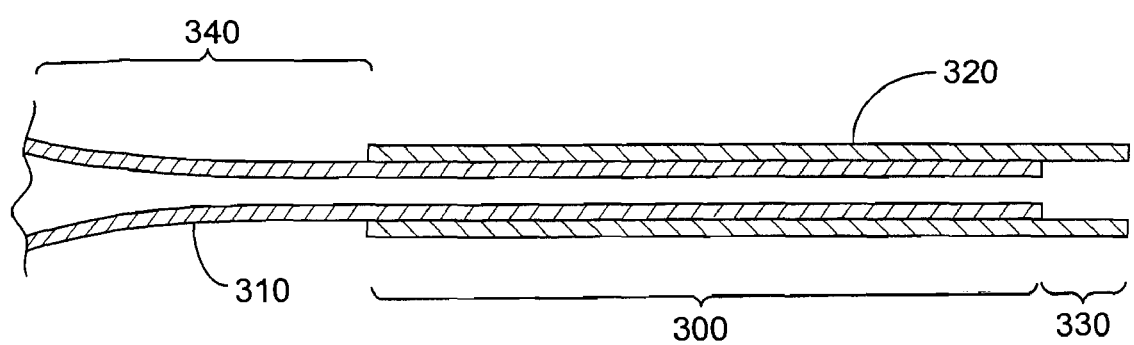
FIG. 3 is a cross-sectional side view of an embodiment of a portion of a stent delivery system.

FIG. 3 is an illustration of the lap weld 300 formed between the distal inner portion 310 and the tip 320. In regions 330 and 340, where there was no overlap between the components, distal inner portion 310 and tip 320 kept their original color (i.e., green and pink, respectively). However, the region of lap weld 300, where there was overlap between the components, was purple.

OTHER EMBODIMENTS

While certain embodiments have been described, the invention is not so limited. As an example, the above-described process can be used to form a bond (e.g., a lap weld, a butt weld) between two medical device components that are of the same color. For example, a lap weld can be formed between two medical device components of the same color by forming an overlap region between the two components, and viewing the overlap region with the above-described apparatus 200. The overlap region can appear as a darker region than the non-overlapped regions of the medical device components, because of the thickness of the overlap region relative to the individual thicknesses of the non-overlapped regions.

Figure 4:
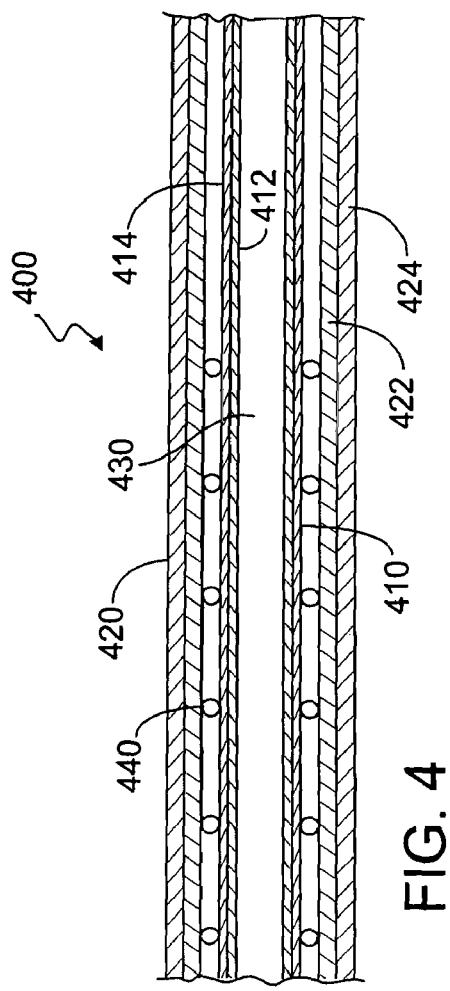
FIG. 4 is a cross-sectional side view of an embodiment of a stent delivery system.

As another example, the above-described process can be used to view an endoprosthesis within an endoprosthesis delivery system (e.g., to determine whether there is an endoprosthesis within the system). For example, and referring now to FIG. 4, the process can be used to view a self-expanding stent 440 in a stent delivery system 400. Stent delivery system 400 includes an inner catheter 410 and a colored retractable sheath 420. Inner catheter 410 is a tube with a lumen 430 that is sized for delivery over a guidewire. Stent 440 (formed of, e.g., a metal) is carried on a distal portion of inner catheter 410. Sheath 420 covers stent 440 during delivery, and can be retracted to expose stent 440 for expansion at a treatment location within a body lumen such as a blood vessel. As shown in FIG. 4, inner catheter 410 includes an inner layer 412 and an outer layer 414. Inner layer 412 can be formed of a relatively low friction polymer to facilitate delivery over a guidewire. Outer layer 414 can include a nanocomposite material. Sheath 420 also includes an inner layer 422 and an outer layer 424. Inner layer 422 can be formed of a low friction polymer that facilitates sliding motion over stent 440 during retraction of sheath 420. Outer layer 424 can include a nanocomposite material. Examples of nanocomposite materials include polyamide 12 (e.g., Nylon 12-based materials). In some embodiments, a sheath and/or a catheter can be formed of only one layer. A suitable stent is a self expanding or balloon expandable stent. In the case of a balloon expandable stent, the stent is carried over a balloon mounted on the inner catheter. Further discussion of a delivery system for a self-expanding stent is described, for example, in Raeder-Devens et al., US 2003/0050686, the entire contents of which are hereby incorporated by reference.

Figure 5:
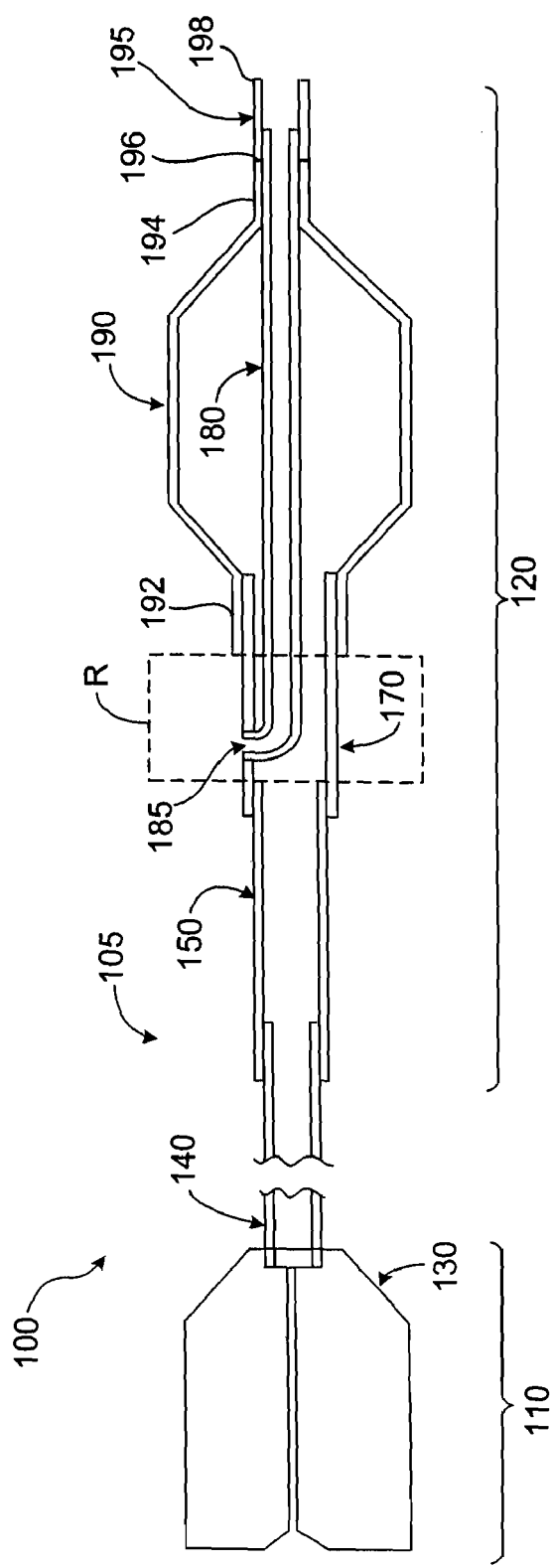
FIG. 5 is a cross-sectional side view of the balloon catheter of FIG. 1A.

As an additional example, the above-described process can be used to view other regions of a balloon catheter. For example, FIG. 5 shows balloon catheter 100 from FIG. 1A. Region "R" defines a section of balloon catheter 100, sometimes known as the "septum", that includes distal outer portion 170 and distal inner portion 180. The above-described process can be used, for example, to view the thicknesses of the components of the septum. In some embodiments, if the components of the septum are too thin, then region "R" of balloon catheter 100 can be relatively weak, which can lead to buckling or kinking Thus, the above-described process can be used to determine whether a catheter has a relatively weak section.

As a further example, in some embodiments, other forms of emitted and detectable energy, such as x-rays, can be used (in addition to, or as an alternative to, visible light and infrared radiation) to determine the extent of overlap between medical device components. The signal of the energy that is emitted can change as the energy passes through and/or bounces off of the polymer components being aligned.

As an additional example, while a dome light has been shown for providing reflective light, in some embodiments, a different type of reflective light source can be used. For example, the reflective light source can be a Broad Area Linear Array (from Advanced Illumination, Rochester, Vt.), an axial array such as the Axial Diffuse Illuminator (from Advanced Illumination, Rochester, Vt.), a diffuse dome illuminator, a dark field illuminator, or a spotlight. In certain embodiments, multiple reflective light sources can be used. The type of reflective light source and/or number of reflective light sources used can depend, for example, on the desired intensity, wavelength, diffusivity, and/or angle of incidence for the reflective light.

All publications, applications, references, and patents referred to above are incorporated by reference in their entirety.

Other embodiments are within the claims.

What is claimed is:

1. A method of making a catheter, the method comprising:
   overlapping a first component of the catheter and a second component of the catheter to provide an overlap region wherein the first component is a first color and the second component is a second color different from the first color;
   applying infrared and visible light to the overlap region to provide contrast between the components;
   detecting the contrast and aligning the first and second components based on the contrast to provide a desired amount of overlap; and
   forming a lap weld between the first and second components.

2. The method of claim 1, wherein the lap weld has a length of from about 3.0 millimeters to about 5.0 millimeters.

3. The method of claim 1, wherein the lap weld has a thickness of from about 0.0012 inch to about 0.011 inch.

4. The method of claim 1, wherein at least some of the infrared radiation is generated by one or more LED's having a wavelength of from about 800 nanometers to about 1000 nanometers.

5. The method of claim 1, wherein at least some of the visible light is generated by one or more LED's having a wavelength of from about 575 nanometers to about 700 nanometers.

6. The method of claim 5, wherein at least some of the visible light is generated by one or more LED's having a wavelength of from about 491 nanometers to about 575 nanometers.

7. The method of claim 6, wherein at least some of the visible light is generated by one or more LED's having a wavelength of from about 400 nanometers to about 491 nanometers.

8. The method of claim 1,
   wherein the first color corresponds to a light having a wavelength of from about 491 nanometers to about 700 nanometers; and
   wherein the second color corresponds to light having a wavelength of from about 400 nanometers to about 491 nanometers.

9. The method of claim 1, further comprising detecting the infrared radiation and visible light with a charge-coupled device, a CMOS, or an InGaAs photodetector.

10. The method of claim 1, wherein the first component comprises a first polymer and the second component comprises a second polymer different from the first polymer.

11. The method of claim 10, wherein at least one of the first polymer and the second polymer comprises a nylon or a polyether-polyamide block copolymer.

12. The method of claim 1, wherein a contrast between the first component and the second component is more than about ten percent.

13. The method of claim 1, wherein a contrast between the first component and the second component is more than about 20 percent.

14. The method of claim 1, wherein a contrast between the first component and the second component is more than about 30 percent.

* * * * *